US00PP36381P2

(12) United States Plant Patent
Kordes

(10) Patent No.: US PP36,381 P2
(45) Date of Patent: Jan. 14, 2025

(54) HYBRID TEA ROSE PLANT NAMED 'KORclagran'

(50) Latin Name: *Rosa hybrida*
Varietal Denomination: KORclagran

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/667,173

(22) Filed: May 17, 2024

(51) Int. Cl.
*A01H 5/02* (2018.01)
*A01H 6/74* (2018.01)

(52) U.S. Cl.
USPC ..... Plt./138
CPC ..... *A01H 6/749* (2018.05)

(58) Field of Classification Search
USPC ..... Plt./138
CPC ..... A01H 6/749; A01H 5/02
See application file for complete search history.

(56) References Cited

U.S. PATENT DOCUMENTS

PP17,047 P2 8/2006 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'KORclagran', is described. The new variety forms in abundance on a substantially continuous basis attractive, wine-red colored blossoms. The vegetation is vigorous, and the growth habit is very bushy and upright. Attractive glossy, medium green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORclagran'.

STATEMENT REGARDING PRIOR DISCLOSURES BY THE INVENTOR

The first offer for sale of the new variety was June 2023, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of hybrid tea rose plant of the present invention was created by controlled breeding in May 2011, in Offenseth-Sparrieshoop, Germany by artificial pollination wherein two parents were crossed which previously had been studied in the hope that they would contribute the desired characteristics. The female parent (i.e., the seed parent) of the new variety was the 'ADHarman' variety (not patented). The male parent (i.e., the pollen parent) of the new variety was an unnamed breeder seedling (not patented).

The parentage of the new variety can be summarized as follows:

'ADHarman' x unnamed breeder seedling

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of hybrid tea rose plant of the present invention possesses the following combination of characteristics:

(a) forms attractive wine-red colored blossoms,
(b) exhibits a very bushy and upright growth habit, and
(c) provides attractive ornamental glossy, medium green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the new variety provides a rounder, more nostalgic flower shape, and more petals compared to flowers of the 'ADHarman' variety (i.e., the seed parent). Additionally, the new variety produces a single blossom per stem, whereas the unnamed breeder seedling parent (i.e., the pollen parent) produces blossoms in clusters. Moreover, the new variety can be readily distinguished from non-parental related similar varieties. For example, the new variety displays a higher petal count, a more rounded, nostalgic flower shape and a wine-red flower color compared to the pure red flower color of the 'KORcoluma' variety (U.S. Plant Pat. No. 17,047).

The new variety has been named the 'KORclagran' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field in Ellerhoop, Germany in July 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during August, while growing in a one-gallon container on its own roots in a nursery in Cochranville, Pennsylvania.

Botanical classification: *Rosa hybrida* cultivar 'KORclagran'.

Commercial classification: Hybrid Tea.

Plant:

Habit.—Bushy and upright.

*Height*.—Approximately 60.0 cm on average from the top of the soil plane.

*Width*.—Approximately 60.0 cm on average.

Branches:

*Stem color*.—Old wood: Green Group 143C. — young stems: Green Group 143C.

*Length*.—Main stems: approximately 60.0 cm on average. — secondary stems: approximately 30.0 cm on average.

*Diameter*.—Main stems: approximately 6.0 mm on average. — secondary stems: approximately 3.0 mm on average.

*Thorns*.—Amount: moderate, 3 to 4 per internode. — young thorns: length is approximately 5.0 mm on average; width is approximately 5.0 mm on average at point of attachment; and color is Greyed-Yellow Group 160A. —old thorns: length is approximately 7.0 mm on average; width is approximately 5.0 mm on average at point of attachment; and color is Greyed-Orange Group 167A.

Leaflets:

*Number*.—5 and 7.

*Shape*.—Ovate; apex is acute to acuminate; and base is cuneate.

*Arrangement*.—Pinnate.

*Margin*.—Serrate.

*Undulation*.—Moderate.

*Glossiness of upper side*.—Glossy.

*Texture*.—Upper surface: smooth. — under surface: smooth.

*Venation pattern*.—Reticulate.

*Size*.—Terminal leaflet: length is approximately 5.5 cm on average; width is approximately 3.7 cm on average. — lower leaflets: length is approximately 3.5 to 4.0 cm on average; width is approximately 2.5 cm on average. — 5-Leaflet leaf: length is approximately 11.5 cm on average; width is approximately 9.5 cm on average.

Foliage:

*Young foliage*.—Upper surface color: Yellow-Green Group 144A with venation of Greyed-Red Group 178A. — under surface color: Greyed-Red Group 178A with venation of Yellow-Green Group 144A.

*Old foliage*.—Upper surface color. Green Group 137A with indistinguishable venation. — under surface color: Yellow-Green Group 146C with indistinguishable venation.

*Petiole*.—Texture: upper surface is papillate; under surface is smooth. — length: approximately 1.5 cm on average. — width: approximately 1.0 mm on average. — upper surface color. Green Group 137A with Yellow-Green Group 146D on the petiole margins. — under surface color: Yellow-Green Group 146B.

*Rachis*.—Length: approximately 2.0 cm on average. — width: approximately 1.0 mm on average. — upper surface color: Green Group 137A. — under surface color: Yellow-Green Group 146C.

*Stipules*.—Length: approximately 1.5 cm on average. — width: approximately 5.0 mm on average. — margin: entire to erose. — upper surface color. Yellow-Green Group 146C. — lower surface color. Yellow-Green Group 146C.

Inflorescence:

*Number of flowers*.—About 10 to 12 blooms on average on a plant at once.

*Number of blossoms per stem or in a cluster*.—Typically 1 bloom per stem on average.

*Peduncle*.—Color. Yellow-Green Group 146B. — diameter. approximately 5.0 mm on average. — length: approximately 5.0 cm on average. — surface texture: hispidulous.

*Sepals*.—Number: 5. — upper surface color and texture: Yellow-Green Group 146B and Red-Purple Group 60A, hispidulous. — under surface color and texture: Green Group 143D, puberulent. — size: length is approximately 2.5 cm to 3.5 cm on average; width is approximately 1.0 cm on average. — margin: entire with extensions on most sepals measuring approximately 6.0 mm in length and 1.0 mm in width on average. — apex: acute to aristate. — base: truncate as it joins the receptacle.

*Buds*.—Shape: ovoid. — size: length is approximately 2.0 cm on average; width is approximately 2.0 cm on average. — color (when opening): Red-Purple Group 59A toward the apex fading to Red-Purple Group 60C and Red-Purple Group 61B toward the base.

*Flower*.—Form: very double, cuplike. — profile: concave as it opens and then outer petals are convex as the bloom ages and opens further. — diameter. approximately 8.0 cm on average. — height: approximately 5.0 cm on average. — duration: on the plant approximately 10 to 12 days. — petal color when first and fully opened: upper surface is Red-Purple Group 61B with a basal spot of Greyed-Yellow Group 160A; under surface is Red-Purple Group 67C with a basal spot of Greyed-Yellow Group 160C. — petal color at end of bloom: upper surface is Red-Purple Group 58A with a distinct basal spot of Greyed-Yellow Group 160A; under surface is Red-Purple Group 61C with a basal spot of Greyed-Yellow Group 160C. — petals reflex one by one: yes.

*Fragrance*.—Very slight sweet scent.

*Petal*.—Number: 75 on average. — drop: average for the type. — length: approximately 3.5 cm on average. — width: approximately 3.0 to 3.5 cm on average. — overall shape: broadly obovate. — margin: entire with moderate undulation. — apex shape: rounded to slightly cuspidate. — base shape: cuneate.

*Petaloids*.—Number. approximately 6 on average. — length: approximately 2.2 cm on average. — width: approximately 7.0 mm on average. — color: upper and under surfaces are Red-Purple Group 61C with a very small basal spot of Greyed-Yellow 160B. — margin: entire. — shape: ovate. — apex: rounded. — base: cuneate.

*Stamen*.—Number. approximately 30. — anthers: number is approximately 30; color is Yellow-Orange Group 21D; length is approximately 1.0 mm on average; and shape is oval. — filaments: length is approximately 5.0 mm on average and color is White Group 155A.

*Pistils*.—Arrangement: separate and free. — number. approximately 32. — style: length is approximately 8.0 mm on average and color is Greyed-Yellow Group 160C. — stigma: diameter is approximately 1.0 mm on average; shape is fan shaped; color is Greyed-Orange Group 163A.

*Receptacle*.—Diameter: approximately 8.0 mm on average. — depth: approximately 6.0 mm on average. — shape: urn shaped. — color: Yellow-Green Group 144A. — surface texture: smooth.

*Pollen*.—Amount: sparse. — color. Yellow-Orange Group 20A.

*Hips/seed*.—None observed.

Development:

*Vegetation*.—Glossy, medium green, vigorous and strong.

*Blossoming*.—Abundant and substantially continuous from spring through frost; typically, in bloom outdoors from May to November in Southeastern Pennsylvania.

*Resistance to diseases*.—Excellent resistance for black spot (*Diplocarpon rosae*), powdery mildew (*Sphaerotheca pannosa*) and rust (*Phragmidium* sp.).

*Hardiness*.—Hardy to USDA Zone 6; further hardiness testing is in progress.

The new 'KORclagran' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of hybrid tea rose plant named 'KORclagran' characterized by the following combination of characteristics:

(a) forms attractive wine-red colored blossoms, (b) exhibits a very bushy and upright growth habit, and (c) provides attractive ornamental glossy, medium green foliage; substantially as herein shown and described.

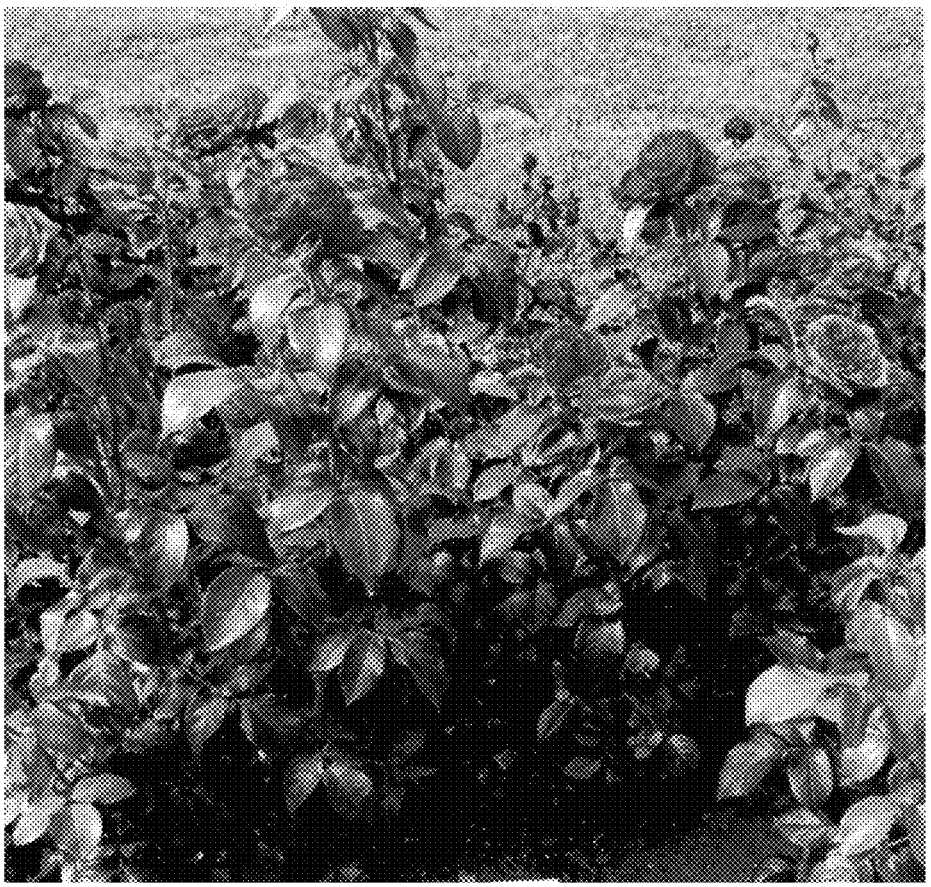

* * * * *